US010328197B2

(12) United States Patent
Horvath et al.

(10) Patent No.: US 10,328,197 B2
(45) Date of Patent: Jun. 25, 2019

(54) PEN NEEDLE TO FACILITATE MANIPULATION BY USERS HAVING PHYSICAL OR VISUAL IMPAIRMENT (75) Inventors: Joshua Horvath, Sparta, NJ (US); Adam Gold, Scarsdale, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/138,304

(22) PCT Filed: Feb. 4, 2010

(86) PCT No.: PCT/US2010/000303
§ 371 (c)(1),
(2), (4) Date: Oct. 12, 2011

(87) PCT Pub. No.: WO2010/090733
PCT Pub. Date: Aug. 12, 2010

(65) Prior Publication Data
US 2012/0022459 A1 Jan. 26, 2012

Related U.S. Application Data (60) Provisional application No. 61/150,678, filed on Feb. 6, 2009.

(51) Int. Cl.
*A61M 5/00* (2006.01)
(52) U.S. Cl.
CPC ......... *A61M 5/002* (2013.01); *A61M 2205/58* (2013.01); *A61M 2205/582* (2013.01)
(58) Field of Classification Search
CPC .. A61M 5/002; A61M 5/3202; A61M 5/3205; A61M 5/321; A61M 5/3213;
(Continued)

(56) References Cited

U.S. PATENT DOCUMENTS 3,380,450 A * 4/1968 Adelberger ............. A61M 5/28
604/117
3,989,045 A * 11/1976 Van Eck ............... A61M 5/282
604/192
(Continued)

FOREIGN PATENT DOCUMENTS

CA 2337557 A1 9/2001
CA 2337557 A1 9/2001
(Continued)

OTHER PUBLICATIONS

Supplementary European Search Report for Application No. EP 10 73 8853 dated Jun. 21, 2012.
(Continued)

*Primary Examiner* — Shefali D Patel
(74) *Attorney, Agent, or Firm* — Dickinson Wright PLLC (57) ABSTRACT A pen needle (501) includes a hub (531) and a needle (521) fixedly connected to the hub (531). An outer cover (511) removably receives the hub (531) and the needle (521). The outer cover (511) has a first gripping member (515) to facilitate removal of the outer cover (511) from the hub (511). A sealing member (541) is removably connected to the outer cover (511). The sealing member (541) has a second gripping member (543) to facilitate removal of the sealing member (541) from the outer cover (511). The first and second gripping members facilitate manipulation of the pen needle by a user with reduced dexterity or a physical or visual impairment.

16 Claims, 7 Drawing Sheets (58) Field of Classification Search
CPC ........ A61M 2205/58; A61M 2205/582; A61M 2205/586; A61M 5/3243; A61M 5/3245; A61M 2005/3254
USPC ................ 128/919; 206/363, 364, 365, 366; 604/506, 171, 172, 192, 198, 199, 263, 604/265, 272
See application file for complete search history.

(56) References Cited

U.S. PATENT DOCUMENTS

| | | | |
|---|---|---|---|
| 4,085,737 A * | 4/1978 | Bordow | A61B 5/1405 600/576 |
| 5,437,647 A | 8/1995 | Firth | |
| 5,501,676 A * | 3/1996 | Niedospial | A61J 1/2096 604/403 |
| 5,709,663 A | 1/1998 | Younkes | |
| 5,941,853 A | 8/1999 | Collins | |
| 5,941,857 A | 8/1999 | Nguyen | |
| 6,485,469 B1 | 11/2002 | Stewart | |
| 2003/0014018 A1 | 1/2003 | Giambattista | |
| 2003/0168365 A1* | 9/2003 | Kaern | 206/364 |
| 2006/0032769 A1* | 2/2006 | Erickson et al. | 206/365 |
| 2006/0229562 A1 | 10/2006 | Marsh et al. | |
| 2007/0149924 A1 | 6/2007 | Marsh | |
| 2009/0012478 A1 | 1/2009 | Weston | |

FOREIGN PATENT DOCUMENTS

| | | | |
|---|---|---|---|
| CA | 2625041 A1 | 4/2007 | |
| EP | 1138338 | 10/2001 | |
| EP | 1138338 A1 * | 10/2001 | .......... A61M 5/3213 |
| JP | 2002505597 | 2/2002 | |
| JP | 2002543931 | 12/2002 | |
| JP | 2005-516691 A | 6/2005 | |
| JP | 2005532129 | 10/2005 | |
| WO | WO 9311814 A1 * | 6/1993 | .......... A61M 5/3213 |

OTHER PUBLICATIONS

Japanese Office Action issued in Japanese Application No. 2011-540686 dated Sep. 25, 2013.
Canadian Office Action dated Mar. 24, 2017 which issued in the counterpart Patent Application No. 2,751,564.
European Office Action dated Nov. 7, 2016 which issued in the counterpart Patent Application No. 10 738 853.0.

* cited by examiner

PEN NEEDLE TO FACILITATE MANIPULATION BY USERS HAVING PHYSICAL OR VISUAL IMPAIRMENT

CROSS REFERENCE TO RELATED APPLICATION

This application is the national stage under 35 U.S.C. § 371 of International Application No. PCT/US2010/000303, filed Feb. 4, 2010, which claims the benefit under 35 U.S.C. § 119(e) of U.S. Provisional Application Ser. No. 61/150,678, filed Feb. 6, 2009, the entire content of which is hereby incorporated by reference.

FIELD OF THE INVENTION

The present invention relates generally to a pen needle that facilitates manipulation by a user with reduced dexterity or a physical or visual impairment. More particularly, the present invention generally relates to a pen needle for a drug delivery device that facilitates medication injections for a user with reduced dexterity or a physical or visual impairment.

BACKGROUND OF THE INVENTION

Insulin and other injectable medications are commonly given with drug delivery devices, such as a drug delivery pen, whereby a disposable pen needle is attached to facilitate drug container access and allow fluid egress from the container through the needle into the patient.

As technology and competition advance, driving the desire for shorter, thinner, less painful, and more efficacious injections, the design of the pen needle and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

Figure 1:
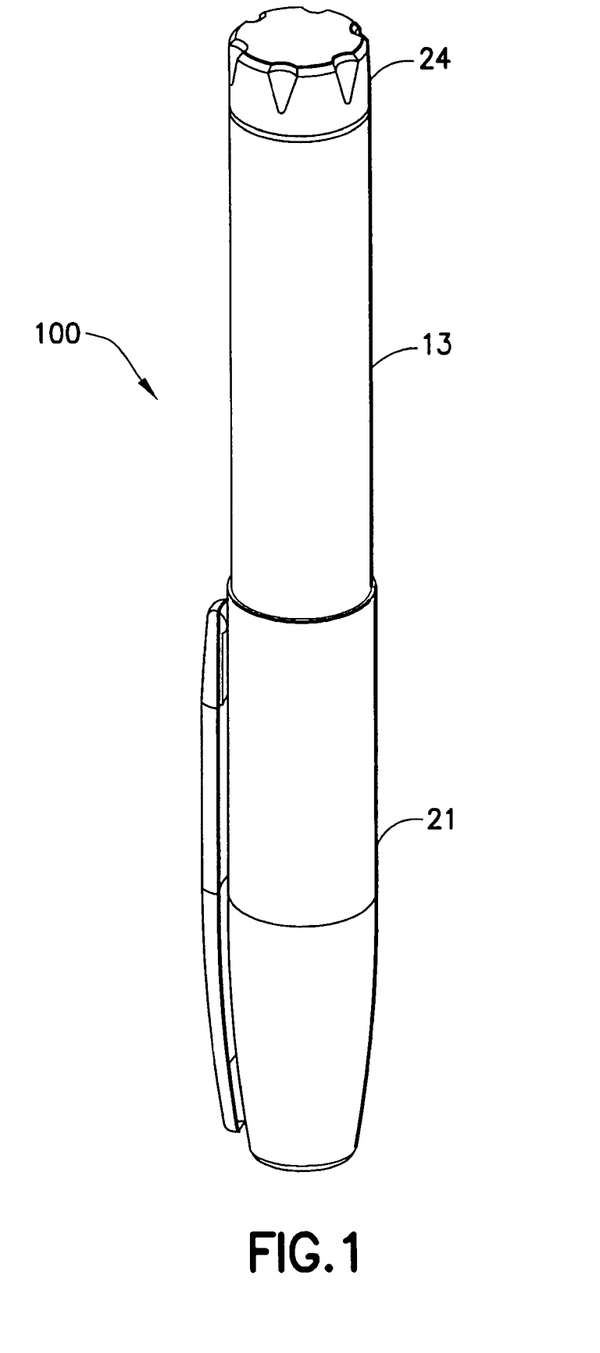
FIG. 1 is a perspective view of an assembled drug delivery pen.
Figure 2:
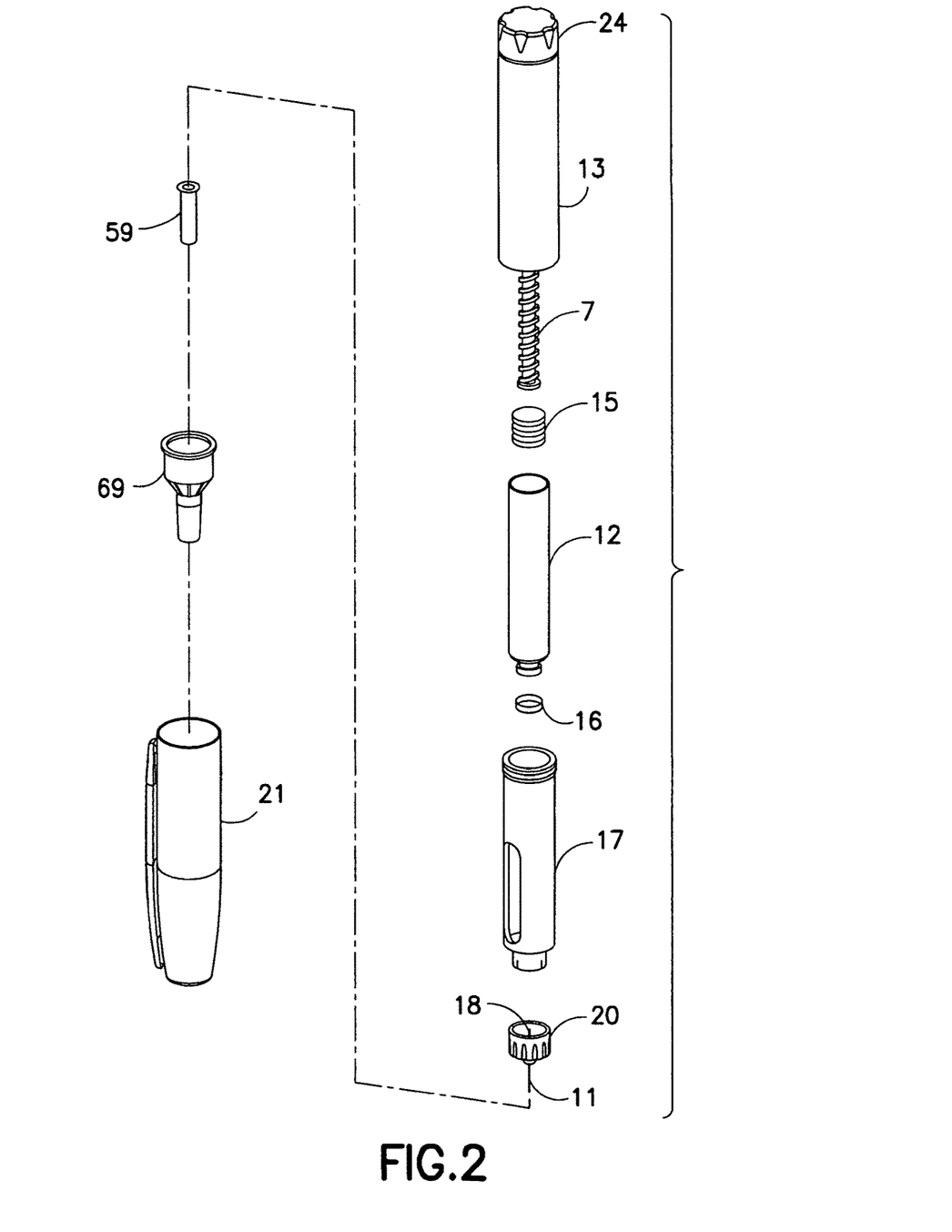
FIG. 2 is an exploded perspective view of the components of the drug delivery pen of FIG. 1.

Drug delivery devices, such as the exemplary drug delivery pen 100 shown in FIGS. 1 and 2, can be designed for subcutaneous, as well as intradermal, injections and typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge 12. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

Figure 3:
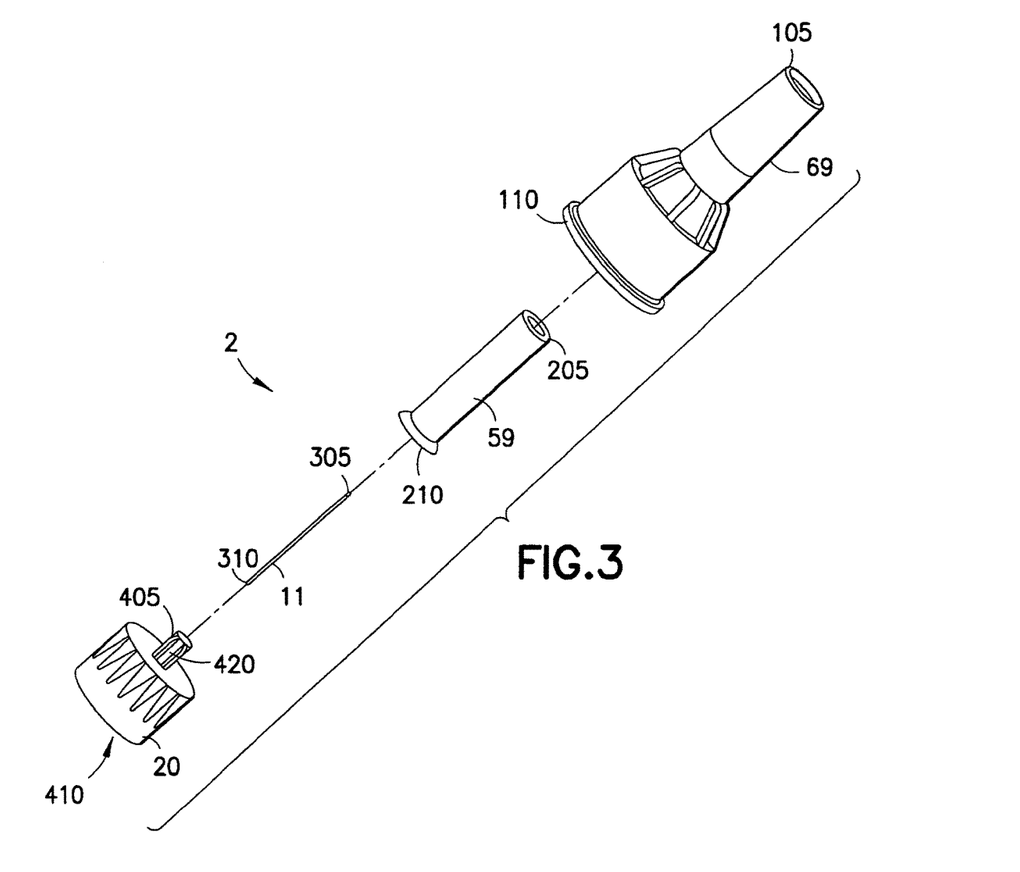
FIG. 3 is an exploded perspective view of a pen needle of the drug delivery pen of FIG. 1.

An exploded perspective view of a pen needle 2 of an exemplary drug delivery pen is shown in FIG. 3. The pen needle 2 includes the cover (outer shield) 69, an inner shield 59, a needle cannula 11, and a hub 20. A proximal end 310 of the needle cannula 11 is inserted into a center opening in the distal (patient) end 405 of the hub 20 until a predetermined length of the distal (patient) end 305 of the needle cannula 11 remains extended. The needle cannula 11 is secured by epoxy or adhesive in the distal end 405 of the hub 20 within the hub protrusion 420.

To protect users from injury and the needle cannula 11 from being damaged, the inner shield 59 covers the exposed portion of the needle cannula 11. The open proximal end 210 of the inner shield 59 is placed over the exposed portion of the needle cannula 11. The open proximal end 110 of the cover 69 envelops the inner shield 59, needle cannula 11, and hub 20.

The distal end 105 of the cover 69 is closed to prevent contamination and damage to the inner components of the pen needle 2, and to prevent injury to anyone who may handle it prior to use. The proximal end 410 of the hub 20 is typically covered by a sanitary paper or foil cover or label (not shown) glued on an end 110 of the cover 69. The pen needle is then ready for shipment to a user. When the user is ready to use the pen needle, the sanitary cover (not shown) is removed from the cover 69, the hub 20 is screwed onto a lower housing 17 of a standard pen 100 (FIGS. 1 and 2), and the cover 69 and shield 59 are separately removed from the hub 20/cannula 11 subassembly by a pulling action. The distal end 205 of the inner shield 59 is closed to cover the distal end 305 of the needle cannula 11 after the cover 69 is removed to protect the user from an accidental needle stick. The inner shield 59 is then removed to access the needle cannula 11. Thus, two separate pulling actions are required to remove both the cover 69 and the shield 59.

Existing pen needles do not have provisions for users with visual or physical impairment or with limited dexterity. Pen needles are relatively small devices, and include a hub and needle rigidly fixed thereto, an inner shield, an outer cover and a sanitary cover or label, as described above. The largest part of the pen needle is the outer cover, which typically has an outer diameter of 0.6 inches and an overall length of 1.2 inches. The label is typically attached to the outer cover by heat sealing and considerable dexterity is required to remove the label. Thus, a need exists to provide a pen needle that facilitates manipulation by users with physical or visual impairment or with limited dexterity.

Existing drug delivery pens are disclosed in U.S. Patent Application Publication Nos. 2006/0229562 to Marsh et al., which was published on Oct. 12, 2006, and 2007/0149924 to R. Marsh, which was published on Jun. 28, 2007, the entire contents of both of which are hereby incorporated by reference.

SUMMARY OF THE INVENTION

In accordance with an aspect of the present invention, an outer cover of a pen needle assembly has increased surface area for gripping by a user.

In accordance with another aspect of the present invention, a label tab has increased surface area to facilitate removal thereof by a user.

In accordance with another aspect of the present invention, a label tab has an opening therein to facilitate removal thereof by a user.

The foregoing objects are basically attained by providing a pen needle including a hub and a needle fixedly connected to the hub. An outer cover removably receives the hub and the needle. The outer cover has a first gripping member to facilitate removal of the outer cover from the hub. A sealing member is removably connected to the outer cover. The sealing member has a second gripping member to facilitate removal of the sealing member from the outer cover.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

The following description and details of exemplary embodiments of the present invention, while generally disclosed in a typical drug delivery pen, as shown in FIGS. 1-3, could more broadly apply to a needle and hub assembly for use in conjunction with, or incorporated onto, other injection devices, such as syringes, autoinjectors and infusion devices.

Figure 4:
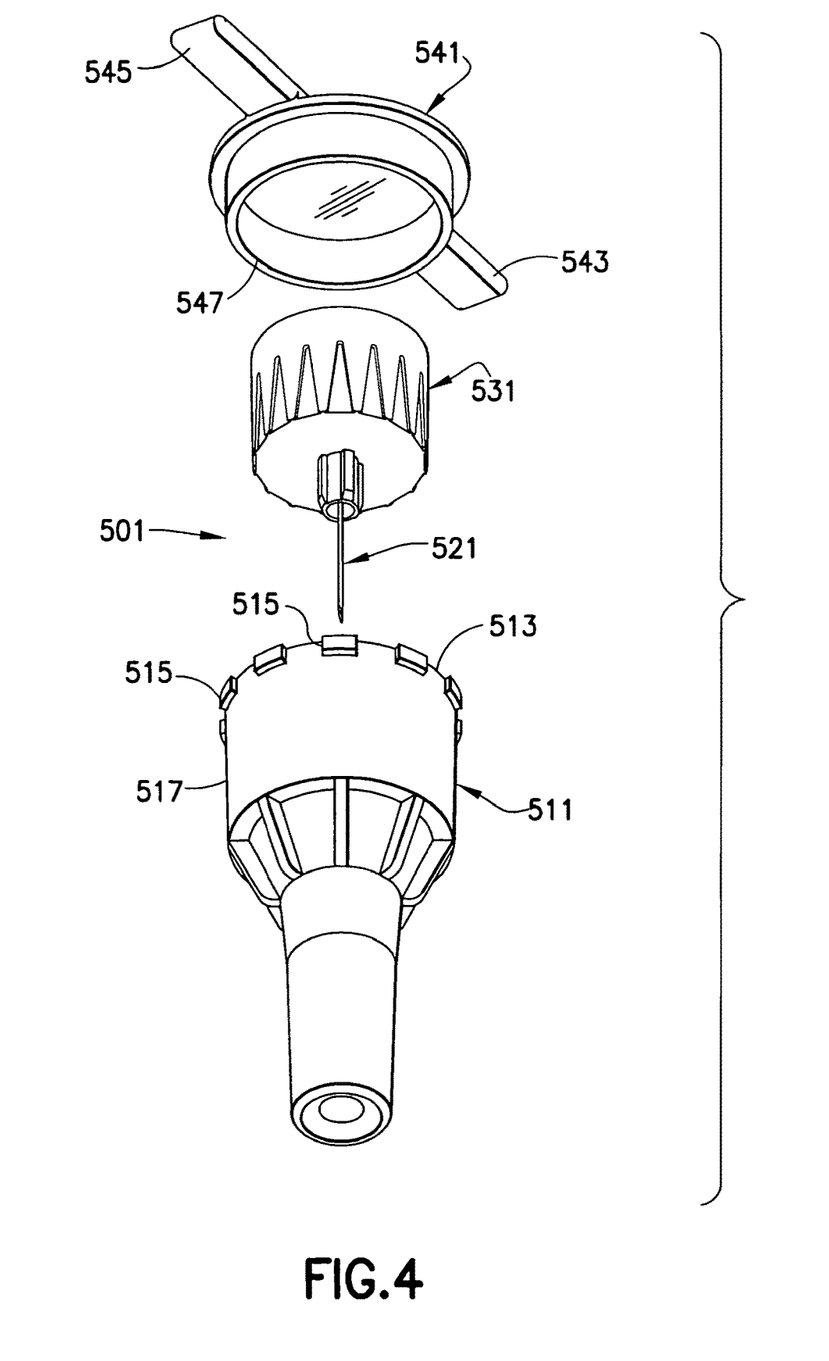
FIG. 4 is an exploded perspective view of a pen needle according to an exemplary embodiment of the present invention in which an outer cover has a cut lip and a cap having wings is connected to the outer cover.

In an exemplary embodiment of the present invention shown in FIG. 4, a pen needle 501 includes an outer cover 511, a needle 521, a hub 531 and a sealing member or cap 541. The hub 531 is disposed within the outer cover 511, such as by a friction fit, thereby shielding the needle 521. The cap 541 is connected to an end 513 of the outer cover 511 to seal the needle 521 and hub 531 within the outer cover. The cap 541 has a rim or skirt 547 that fits either inside or outside the outer cover 511 with a friction fit. Preferably, the skirt 547 fits over the outside of the outer cover 511 to avoid interfering with the hub 531 disposed inside the outer cover. To provide a tamper-evident seal between the cap 541 and the cover 511, an adhesive label, heat sealing or heat staking may be used across the joint between the cap 541 and the cover 511.

The cap 541 is preferably made of a plastic material. Wings 543 and 545 extend outwardly from the cap 541 to facilitate removal of the cap from the outer cover 511. Preferably, as shown in FIG. 4, the wings 543 and 545 extend in substantially opposite directions from each other.

A plurality of projections 515 are circumferentially disposed on an outer surface 517 of the outer cover 511 proximal the end 513 thereof. The projections 515 facilitate gripping the outer cover 511 during installation and removal of the pen needle assembly 501 (without the cap 541) from the drug delivery pen.

Figure 5:
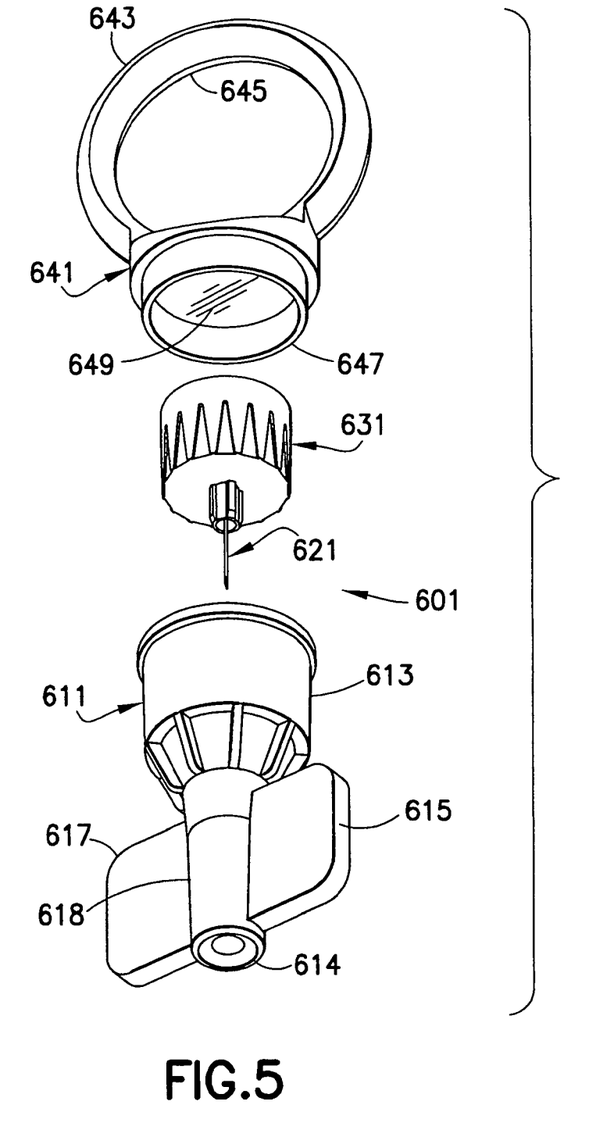
FIG. 5 is an exploded perspective view of a pen needle according to another exemplary embodiment of the present invention in which an outer cover has wings and a cap having a ring is connected to the outer cover.

In another exemplary embodiment of the present invention shown in FIG. 5, a pen needle 601 includes an outer cover 611, a needle 621, a hub 631 and a sealing member or cap 641. The hub 631 is disposed within the outer cover 611, such as by a friction fit, thereby shielding the needle 621. The cap 641 is disposed over a first end 613 of the outer cover 611 to seal the needle 621 and hub 631 within the outer cover. The cap 641 has a rim or skirt 647 that fits either inside or outside the outer cover 611 with a friction fit. The interior of the rim or skirt 647 is closed by an end wall 649 to define a closed cavity for sealing the outer cover 611. Preferably, the skirt 647 fits over the outside of the outer cover 611 to avoid interfering with the hub 631 disposed inside the outer cover.

The cap 641 is preferably made of a plastic material. A ring-like projection 643 extends outwardly from the cap 641 to facilitate removal of the cap from the outer cover 611. The ring-like projection 643 has an opening 645 therein to facilitate gripping the ring-like projection. Preferably, as shown in FIG. 5, the ring-like projection extends in a direction substantially parallel to the axis of the needle 621.

Wings 615 and 617 extend outwardly from the narrow nose portion 618 of the outer cover 611 proximal a second end 614 thereof. The wings 615 and 617 facilitate gripping the outer cover 611 during installation and removal of the pen needle assembly 601 (without the cap 641) from the drug delivery pen, thereby reducing the force required to be exerted by the user. Preferably, as shown in FIG. 5, the wings 615 and 617 extend in a direction substantially parallel to the axis of the needle 621.

Figure 6:
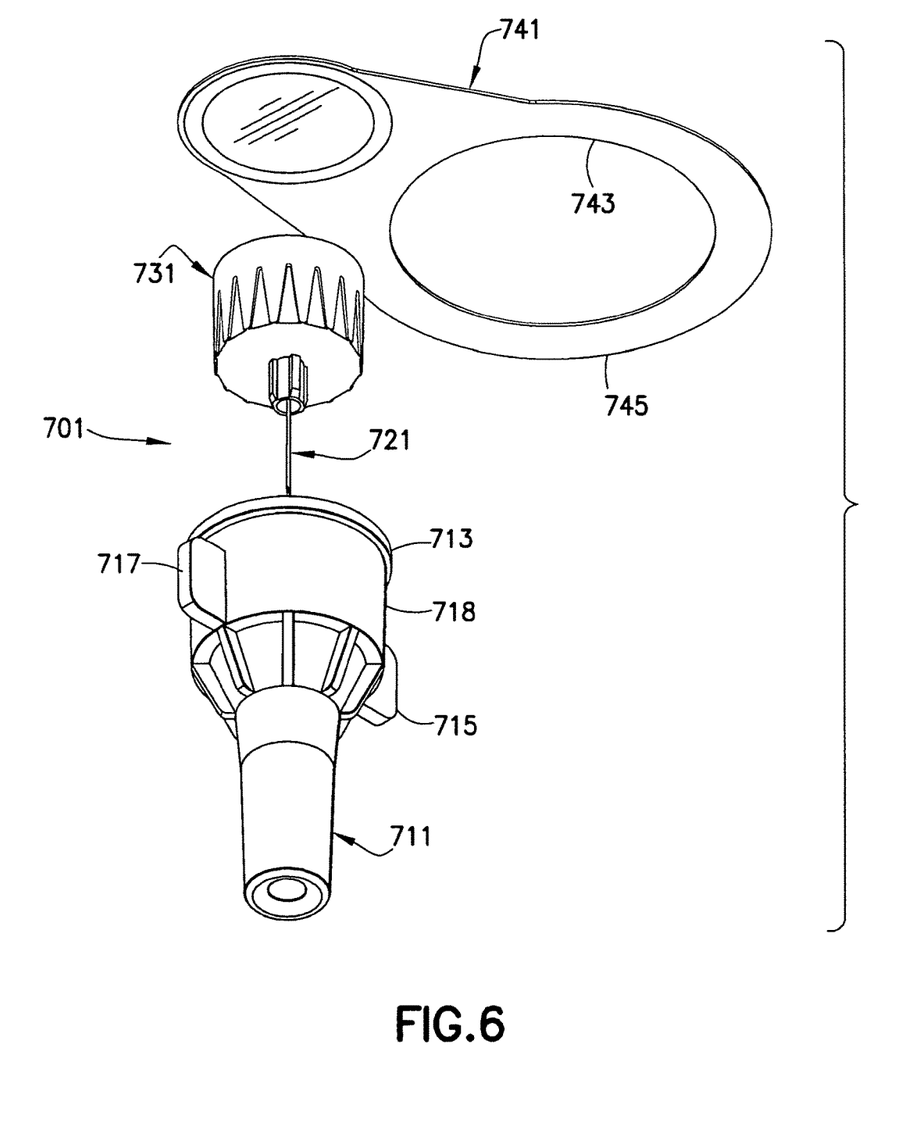
FIG. 6 is an exploded perspective view of a pen needle according to another exemplary embodiment of the present invention in which an outer cover has wings and a label seal having an opening is connected to the outer cover.

In another exemplary embodiment of the present invention shown in FIG. 6, a pen needle 701 includes an outer cover 711, a needle 721, a hub 731 and a sealing member or label 741. The hub 731 is disposed within the outer cover 711, such as by a friction fit, thereby shielding the needle

721. The label 741 is disposed over a first end 713 of the outer cover 711 to seal the needle 721 and hub 731 within the outer cover 711.

The label 741 extends substantially perpendicular to an axis of the needle 721. An opening 743 in a tab 745 of the label 741 facilitates removal of the cap from the outer cover 711. The opening 743 in the tab 745 allows a user to firmly grip the tab 745, thereby facilitating removal of the label 741 by a user with limited dexterity.

Wings 715 and 717 extend outwardly from the wider body portion 718 of the outer cover 711 distal the first end 713 thereof. The wings 715 and 717 facilitate gripping the outer cover 711 during installation and removal of the pen needle 701 (without the label 741) from the drug delivery pen (FIG. 2), thereby reducing the force required to be exerted by the user.

Figure 7:
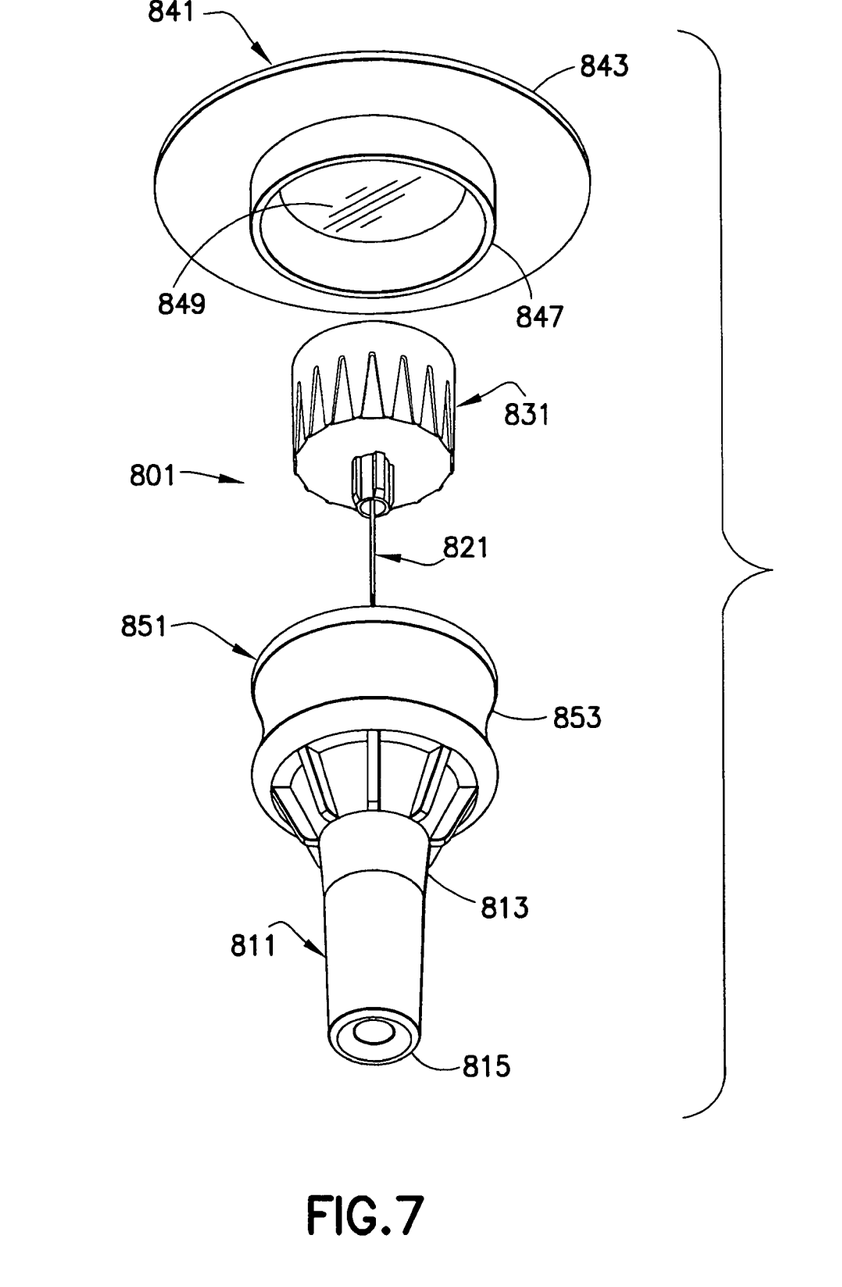
FIG. 7 is an exploded perspective view of a pen needle assembly according to another exemplary embodiment of the present invention in which an outer cover has an overmolded ring and a cap having a gripping base is connected to the outer cover.

In another exemplary embodiment of the present invention shown in FIG. 7, a pen needle assembly 801 includes an outer cover 811, a needle 821, a hub 831 and a sealing member or cap 841. The hub 831 is disposed within the outer cover 811, such as by a friction fit, thereby shielding the needle 821. The cap 841 is disposed over a first end of the outer cover 811 to seal the needle 821 and hub 831 within the outer cover. The cap 841 has a rim or skirt 847 that fits either inside or outside the outer cover 811 with a friction fit. The interior of the rim or skirt 847 is closed by an end wall 849 to define a closed cavity for sealing the outer cover 811. Preferably, the skirt 847 fits over the outside of the outer cover 811 to avoid interfering with the hub 831 disposed inside the outer cover 811.

The cap 841 is preferably made of a plastic material. A base 843 of the cap 841 extends outwardly from the outer cover 811 to facilitate removal of the cap from the outer cover 811 to facilitate gripping of the cap. Preferably, as shown in FIG. 7, the base 843 of the cap 841 extends in a direction substantially perpendicular to the axis of the needle 821 and beyond the widest portion of the outer cover 811.

A rubber overmold 851 is disposed on an outer surface 813 distal the first end 815 of the outer cover 811, as shown in FIG. 7. The overmold 851 facilitates gripping the outer cover 811 during installation and removal of the pen needle 801 (without the cap 841) from the drug delivery pen (FIG. 2), thereby reducing the force required to be exerted by the user. Preferably, the overmold 851 is disposed over the widest portion of the outer cover 811. The overmold 851 preferably is contoured, such as with a valley 853, to further facilitate gripping the outer cover 811.

As shown in FIGS. 4-7, an inner shield is preferably not used because the inner shield is a relatively small part that is difficult for many users to manipulate. Accordingly, an inner shield (59 in FIG. 3) is preferably not used with these exemplary embodiments of the present invention.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A pen needle, comprising:
   a hub;
   a needle fixedly connected to said hub;
   an outer cover having an open end and an outer surface forming a widest portion of said outer cover, said open end configured for removably receiving said hub and said needle, said outer cover having a first gripping member extending outwardly a distance wider than said widest portion of said outer cover to facilitate removal of said outer cover from said hub; and
   a sealing member removably connected to said open end of said outer cover to seal said needle and said hub within said outer cover, said sealing member having a second gripping member to facilitate removal of said sealing member from said outer cover, said second gripping member comprising a first wing and a second wing extending outwardly from said sealing member a distance greater than said widest portion of said outer cover;
   wherein said first gripping member comprises a plurality of projections on said outer surface of said outer cover, each of said plurality of projections extending outwardly a distance greater than said widest portion of said outer cover; and
   wherein said plurality of projections are spaced apart from one another along a circumference of said outer surface of said outer cover.

2. The pen needle according to claim 1, wherein said plurality of projections are disposed proximal said open end of said outer cover that receives said hub, and where said plurality of projections extend radially outward from said widest portion of said outer cover.

3. The pen needle according to claim 1, wherein said first and second wings are diametrically opposed.

4. The pen needle according to claim 1, wherein said plurality of projections comprise first and second wings extending outwardly from said outer surface of said outer cover at said widest portion of said outer cover.

5. The pen needle according to claim 4, wherein said first and second wings of said plurality of projections are disposed proximal an end of said outer cover that receives said hub.

6. The pen needle according to claim 1, wherein said plurality of projections comprise first and second wings disposed proximal a first end of said outer cover spaced from a second end that receives said hub.

7. The pen needle according to claim 1, wherein said sealing member comprises a cap.

8. The pen needle according to claim 1, wherein said second gripping member is spaced from and extends away from said outer cover when said sealing member is connected to said outer cover.

9. A pen needle, comprising:
   a hub;
   a needle fixedly connected to said hub;
   an outer cover for removably receiving said hub and said needle, said outer cover having a first gripping member extending wider than a widest portion of an outer surface of said outer cover to facilitate removal of said outer cover from said hub, wherein said first gripping member comprises an overmolded rubber member disposed over said widest portion of said outer surface of said outer cover, said overmolded rubber member forming an annular recess around said outer cover for gripping said outer cover; and
   a sealing member removably connected to said widest portion of said outer cover to seal said needle and said hub within said outer cover, said sealing member having a second gripping member to facilitate removal of said sealing member from said outer cover.

10. The pen needle according to claim 9, wherein said sealing member comprises a cap.

11. The pen needle according to claim 10, wherein said second gripping member comprises a ring-shaped member extending axially outwardly from said cap.

12. The pen needle according to claim 10, wherein said second gripping member comprises a base extending outwardly from said cap.

13. The pen needle according to claim 9, wherein said overmolded member is disposed proximal an end of said outer cover that receives said hub.

14. A pen needle, comprising:
a hub;
a needle fixedly connected to said hub;
an outer cover having an open end, a closed end, and an outer surface forming a widest portion of said outer cover at said open end, said open end configured for removably receiving said hub and said needle, said outer cover having a first gripping member extending radially outwardly, said first gripping member including a first wing extending radially outward from said closed end of said outer cover and a second wing extending radially outward from said closed end of said outer cover, said first wing and said second wing extending radially outward a distance wider than said closed end and said widest portion of said outer cover to facilitate removal of said outer cover from said hub; and
a sealing member having a body with an annular skirt extending from a first end of said body and removably connected to said open end of said outer cover to seal said needle and said hub within said outer cover, said sealing member having a ring-shaped second gripping member to facilitate removal of said sealing member from said outer cover, said ring-shaped second gripping member extending axially from a second end of said body of said sealing member and having a radial width extending outwardly from said body of said sealing member a distance greater than said widest portion of said outer cover, and said first wing and said second wing extending radially outward a distance wider than said body of said sealing member.

15. The pen needle of claim 14, wherein said sealing member comprises a car.

16. A pen needle, comprising:
a hub;
a needle fixedly connected to said hub;
an outer cover having an open end, a closed end, and an outer surface forming a widest portion of said outer cover at said open end, said open end configured for removably receiving said hub and said needle, said outer cover having a first gripping member, said first gripping member including a first wing extending radially outward from said outer cover at said open end of said outer cover and a second wing extending radially outward from said outer cover at said open end of said outer cover, said first wing and said second wing extending radially outward a distance wider than said open end and said widest portion of said outer cover to facilitate removal of said outer cover from said hub; and
a sealing member having a planar configuration attached to said open end of said outer cover to seal said needle and said hub within said outer cover, said sealing member lying in a plane substantially perpendicular to an axis of said outer cover and having a ring-shaped second gripping member to facilitate removal of said sealing member from said outer cover, said ring-shaped second gripping member extending radially outward from said axis of said outer cover a distance greater than said open end and said widest portion of said outer cover, and wherein said ring-shaped second gripping member has a plane configuration and lies in a plane parallel to said sealing member.

* * * * *